United States Patent
Klemp et al.

(10) Patent No.: US 6,794,557 B1
(45) Date of Patent: Sep. 21, 2004

(54) DISPOSABLE ABSORBENT ARTICLE EMPLOYING AN ABSORBENT COMPOSITE AND METHOD OF MAKING THE SAME

(75) Inventors: Walter V. Klemp, Houston, TX (US); Paul M. Ducker, St. Simons, GA (US); Scott W. Sneed, Decatur, GA (US); Migaku Suzuki, Kanagawa (JP)

(73) Assignee: Associated Hygienic Products LLC

( * ) Notice: Subject to any disclaimer, the term of this patent is extended or adjusted under 35 U.S.C. 154(b) by 0 days.

(21) Appl. No.: 09/615,978

(22) Filed: Jul. 14, 2000

Related U.S. Application Data

(60) Provisional application No. 60/144,345, filed on Jul. 16, 1999.

(51) Int. Cl.⁷ .............................................. A61F 13/15
(52) U.S. Cl. .................. 604/378; 604/368; 604/379; 604/380; 604/385.28; 604/385.101; 442/84
(58) Field of Search ................. 604/368, 374, 604/378, 379, 380, 385.01, 385.101, 385.28, 367, 383, 365, 375, 381, 382, 385.23, 385.24, 385.25; 442/84

(56) References Cited

U.S. PATENT DOCUMENTS

| | | | |
|---|---|---|---|
| 4,041,950 A | * 8/1977 | Jones, Sr. ................... 604/374 |
| 4,055,180 A | 10/1977 | Karami et al. |
| 4,230,113 A | * 10/1980 | Mehta .................. 604/385.09 |
| 4,578,068 A | 3/1986 | Kramer et al. |
| 4,681,577 A | * 7/1987 | Stern et al. ................. 604/378 |
| 4,731,071 A | 3/1988 | Pignuel |
| 5,403,870 A | * 4/1995 | Gross ......................... 523/105 |
| 5,422,169 A | 6/1995 | Roe |
| 5,571,096 A | 11/1996 | Dorbin et al. |
| 5,628,737 A | 5/1997 | Dorbin et al. |
| 5,643,244 A | * 7/1997 | Yamaki et al. ......... 604/385.24 |
| 5,695,324 A | 12/1997 | Weirich |
| 5,736,595 A | 4/1998 | Günther et al. |
| 5,807,367 A | * 9/1998 | Dilnik et al. ................ 604/369 |
| 5,919,179 A | 7/1999 | Faulks et al. |
| 5,961,508 A | * 10/1999 | Mayer et al. ............. 604/385.1 |
| 6,159,190 A | * 12/2000 | Tanaka et al. .......... 604/385.24 |
| 6,258,196 B1 | * 7/2001 | Suzuki et al. ................ 156/176 |
| 6,326,525 B1 | * 12/2001 | Hamajima et al. .......... 604/378 |

FOREIGN PATENT DOCUMENTS

| | | | |
|---|---|---|---|
| EP | 0200409 B1 | 6/1994 | |
| EP | 0947549 A1 | 6/1998 | |
| EP | 0 947549 | * 10/1999 | ............. C08L/1/00 |
| JP | 411047192 A | * 8/1997 | ........... A61F/13/54 |
| JP | 410248872 A | * 9/1998 | ........... A61F/13/15 |
| JP | 411034200 A | * 2/1999 | ........... A61F/13/15 |
| JP | 411137600 A | * 5/1999 | ........... A61F/13/15 |
| JP | 411170414 A | * 6/1999 | ........... A61F/13/46 |
| WO | WO 90/10426 | 9/1990 | |
| WO | WO 98259999 A1 | * 6/1998 | ........... A61L/15/00 |

\* cited by examiner

*Primary Examiner*—John J. Calvert
*Assistant Examiner*—Jacqueline F Stephens
(74) *Attorney, Agent, or Firm*—Alberto Q. Amatong, Jr.; The Morris Law Firm, P.C.

(57) ABSTRACT

A disposable absorbent article includes a topsheet, a backsheet and an absorbent core disposed therebetween. One or more of the backsheet, topsheet, and absorbent core is constructed of an absorbent composite that includes an absorbent layer of hydratable fine fibers in the form of microfibril obtained from cellulose or a derivative thereof and super absorbent polymer (SAP) particles bonded together by the hydratable fibers, and a nonwoven substrate supporting the absorbent layer such as SMS. The absorbent layer is coated over the surface of the nonwoven substrate. The core may include one uniform layer of the absorbent composite or a composite having one layer of the nonwoven substrate and a plurality of segmented absorbent layers applied thereon. In the latter design, the absorbent layers are spaced apart from one another to expose surface sections of the substrate. These non-coated surface sections provide wicking zones which allow room for the absorbent layers to expand and prevent gel blocking.

22 Claims, 11 Drawing Sheets

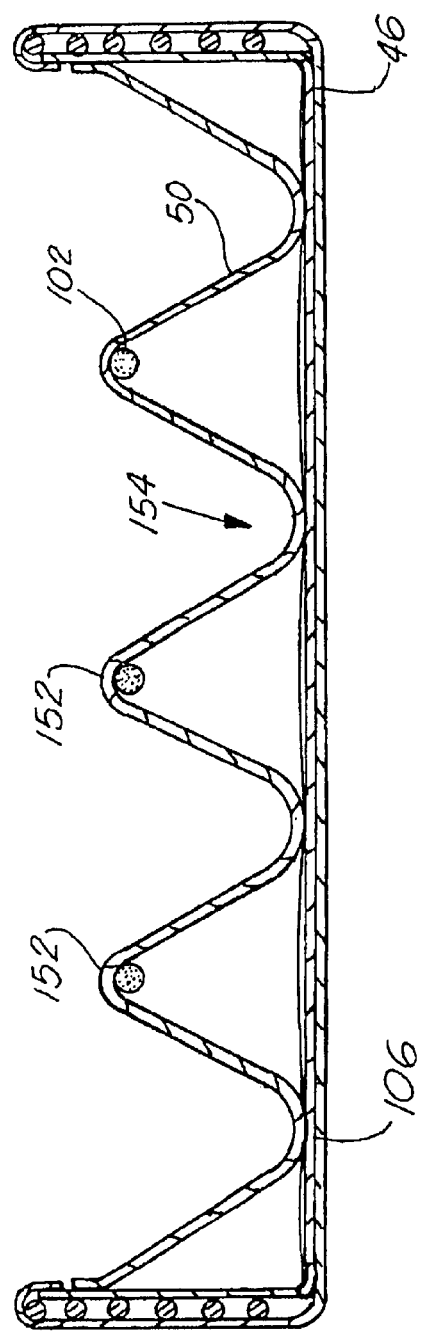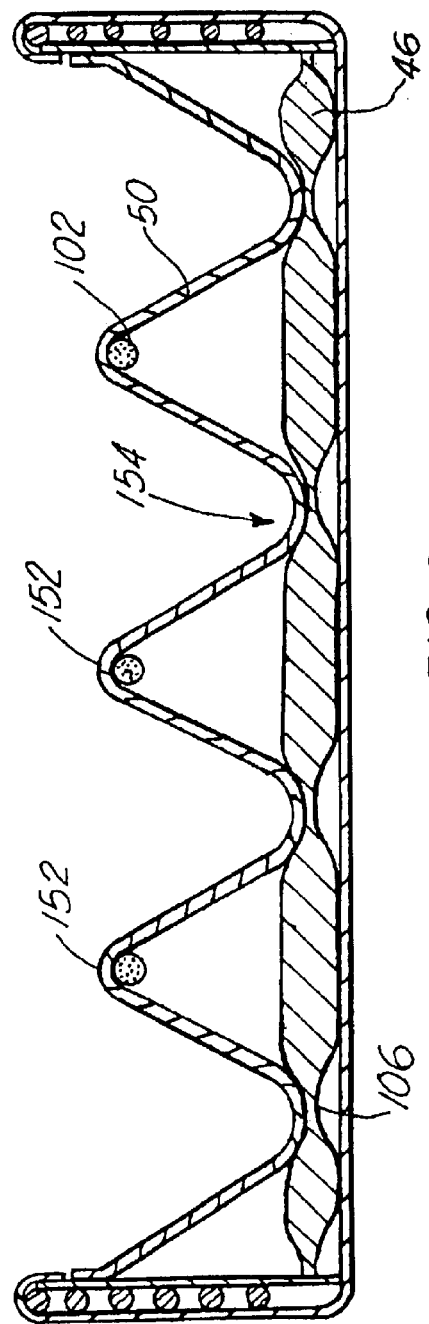

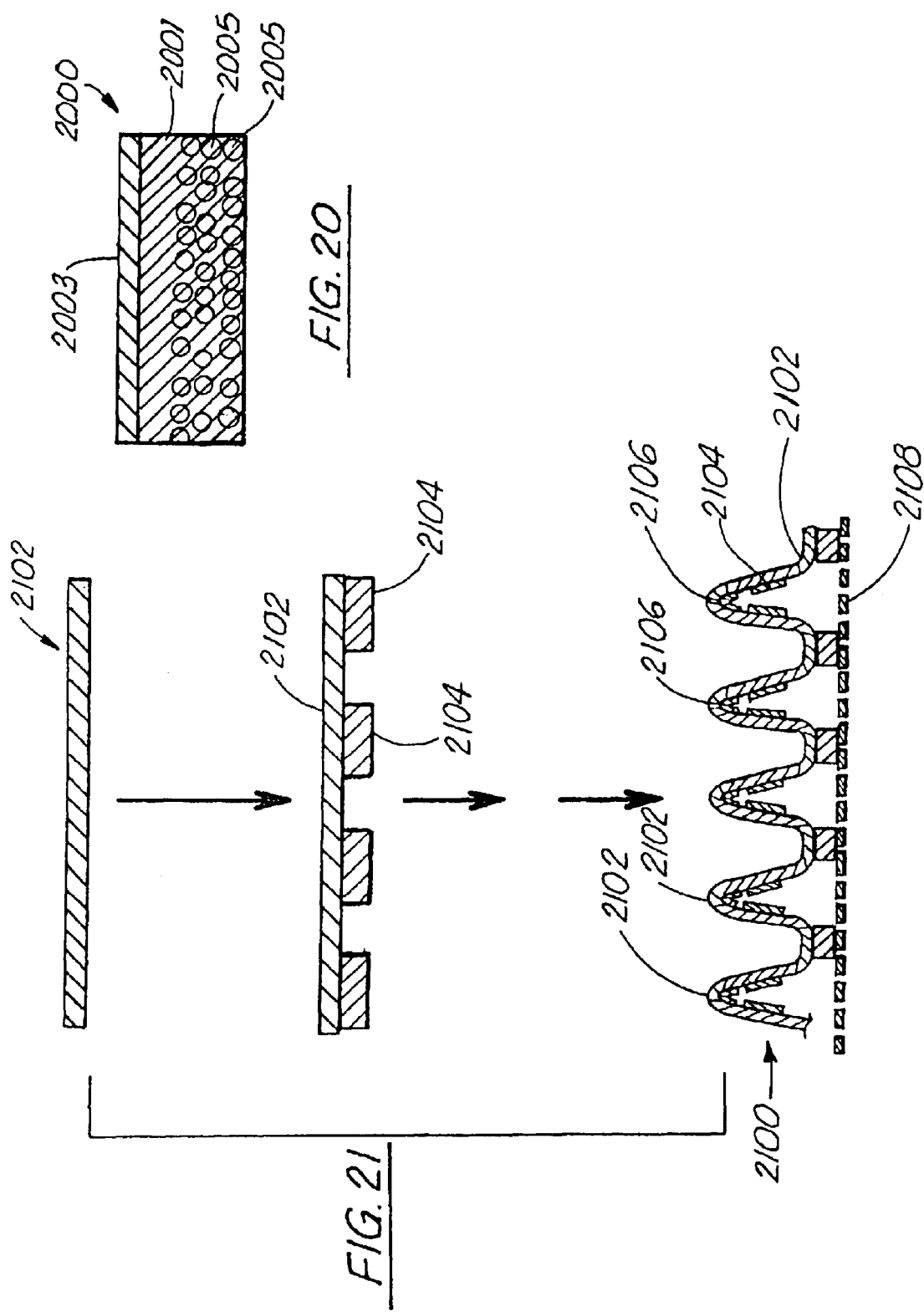

DISPOSABLE ABSORBENT ARTICLE EMPLOYING AN ABSORBENT COMPOSITE AND METHOD OF MAKING THE SAME

The present application claims the benefit of the filing date of U.S. provisional application Ser. No. 60/144,345 filed Jul. 16, 1999 (which is hereby incorporated by reference for all purposes).

BACKGROUND OF THE INVENTION

The present invention relates generally to a disposable absorbent article or garment that employs an absorbent composite as one or more of its structural components. Disposable absorbent articles or garments contemplated by the invention include diapers, training pants, adult incontinence products, feminine hygiene products, and other similar use absorbent products (collectively "disposable absorbent articles"). The use of disposable diapers and training pants has surpassed the use of cloth diapers. Disposable feminine hygiene products are popular because these offer improved comfort and utility to the wearer. Disposable incontinence products, on the other hand, are intended for adults and provide these wearers control and absorption of involuntary bowel and bladder discharge associated with some medical conditions, including those associated with advancing age.

Prior art disposable absorbent articles typically employ three basic structural elements: a fluid permeable topsheet that is placed next to the wearer's skin when the article is worn, a backsheet which forms the outer surface of the diaper, and an absorbent element interposed between the topsheet and the backsheet. The permeable topsheet is designed to allow liquid to pass from the area adjacent the wearer into the area of the core. Topsheets may be constructed from a wide range of liquid and vapor permeable hydrophilic material, and may be used with surface activation agents ("surfactants") to increase its liquid permeability. Surfactants lower the surface tension of the liquid and facilitates the liquid's passage through the topsheet.

The backsheet is typically vapor and liquid impermeable so as to minimize or prevent leakage. For example, the backsheet is often an impermeable film that extends the full width of the article. In some of the more recent designs, a cloth-like outer sheet is added to the film for a more pleasing feel, as the film is positioned to cover only the central portion of the backsheet, and/or in the area most likely to be exposed to liquid. In either design, the film may be made so as to be impermeable or to have some vapor transmission properties, or "breathability," and functions to contain fluids within the absorbent element. Such a two-layer backsheet design, however, contributes to the complexity of any manufacturing process. The articles further include a middle layer of a moisture absorbent core between the topsheet and backsheet. The absorbent core must be able to take up the liquid which passes through the topsheet, and distribute the liquid. The core is designed to retain the distributed liquid.

A typical absorbent core of the prior art is constructed of two components: a high or super absorbent material and an absorbent matrix. Common sources of absorbent materials include numerous compounds of organic materials such as polyvinyl alcohol, polyacrylates, various grafted starches, and cross-linked sodium polyacrylate. These absorbent materials are employed as core material in the form of particles, fibers, foams, and/or layers. The absorbent matrix, on the other hand, is typically provided by de-fiberized wood pulp or similar material. As expected, the majority volume of a prior art absorbent core is taken up by the absorbent matrix and not the absorbent material.

The two-component core design is used primarily because many of the preferred high absorbent materials are incapable of absorbing liquid at the rate or even near the rate at which liquid is typically received by the absorbent article (when worn). Therefore, the absorbent matrix is provided to hold the received liquid and deliver it to the high absorbency material at a rate slower than the rate at which the liquid would otherwise be delivered (absent the absorbent matrix). This allows the high absorbent material more time to fully absorb the liquid.

Another function of the absorbent matrix is to prevent "gel blocking." Gel blocking is the blockage of the interstitial spaces between elements or particles of the high absorbent material and blockage of channels through which the liquid must pass to encounter unsaturated absorbent particles. Such gel blocking can occur as a result of the high absorbency particles or elements swelling upon absorption of liquid and occupying additional volume. The fibers of the matrix prevent "gel blocking" by dispersing the high absorbent particles throughout the matrix, thereby minimizing the potential for particle-to-particle contact.

Although the absorbent matrix does not have the high absorption properties of the high absorbent material, it is recognized as a necessary component in achieving adequate absorbency (measured by both capacity and rate) in prior art core compositions. Achieving optimal absorbency in these core compositions involves not only selecting a suitable high absorbent material, but also identifying the optimal ratio between the high absorbent material and the absorbent matrix. Since the SAP material is typically 2–10 times more absorbent than the pulp material (of the absorbent matrix), one means of providing a thinner, more compact absorbent core is to increase its SAP content and decrease its pulp content. The ratio of SAP content to pulp content is, however, limited by the propensity of higher SAP/pulp ratio compositions to gel block during use. It is generally accepted that an SAP/pulp ratio of 1 is the highest, practical ratio available. Accordingly, this ratio also sets the lower practical limit of the core thickness and thus, of the disposable absorbent article.

SUMMARY OF THE INVENTION

It is, therefore, one of multiple objects of the invention to provide a disposable absorbent article or garment employing an improved absorbent composite therein. According to the invention, such an absorbent composite may be employed as a primary component of the absorbent core, backsheet, topsheet, containment walls or cuffs, and other elements (e.g., an acquisition layer) of the disposable absorbent article, or a combination of two or more of these elements, thereby producing an absorbent article having various advantageous characteristics. Among some of the characteristics which may be exhibited by the inventive disposable absorbent article are improved fit and appearance, improved absorption and liquid containment properties, simpler, more efficient manufacturing process, reduction of components and material sources, and a thinner, more compact construction.

A disposable absorbent article according to the invention includes a topsheet, a backsheet, and an absorbent core disposed therebetween. At least one of the backsheet, topsheet, and absorbent core and/or a combination of these elements (e.g., a backsheet/absorbent core composite or topsheet/absorbent core composite) utilizes an absorbent composite. The absorbent composite is constructed of an absorbent layer (e.g, a low-density layer) of hydratable fine fibers in the form of microfibril obtained from cellulose or a derivative thereof, and absorbent polymer (i.e., SAP) particles bonded together by the hydratable fibers, and a nonwoven substrate (e.g., a high-density layer) supporting the absorbent layer. The absorbent layer is coated upon the nonwoven substrate.

Containment walls including leg cuffs or leg gathers may also utilize the absorbent composite. For example, the article may employ a pair of longitudinally-extending, upstanding cuffs spaced laterally from the core. Each cuff includes a folded portion of the topsheet and a longitudinally-extending absorbent composite secured within the folded portion. The longitudinally-extending absorbent composite also includes an absorbent layer of hydratable fine fibers in the form of microfibril and super absorbent polymer (SAP) particles bonded together by the hydratable fibers and a nonwoven substrate supporting the absorbent layer. In one set of embodiments, the core also includes an absorbent composite, and the core's absorbent composite and the longitudinally extending absorbent composites of the cuffs are sections of one continuous absorbent composite structure. This composite structure is positioned about a crotch region of the article and may be adapted (e.g., by selecting appropriate SAP material specifications) to swell upon wetting so as to substantially gel-block and liquid seal the crotch region. Further, a nonwoven section of the topsheet may provide the nonwoven substrate of the absorbent composite of the containment walls and/or of the absorbent core.

In another aspect of the invention, a backsheet utilizing the absorbent composite preferably includes a low cross link SAP that is adapted to gel block upon wetting. In this way, the backsheet is breathable when dry but the absorbent layer and, thus, the backsheet, is substantially impervious when wet. Such a low cross-link SAP may be a low gel strength SAP having free swell capacities greater than about 40 g/g SAP.

In yet another aspect of the invention and in one set of embodiments, the absorbent core may be formed from a prefabricated sheet of the absorbent composite. In one embodiment, the absorbent composite has a plurality of absorbent layers (e.g., segmented) which are spaced apart from one another such that non-coated surface sections of the substrate are exposed therebetween. The non-coated surface sections form wicking zones between the absorbent layers and allow the absorbent layers room to swell, thereby preventing or minimizing gel blocking and promoting saturation of the absorbent layers. The segments of absorbent layers may be laterally spaced, elongated segments, randomly or equally dispersed (e.g., a staggered pattern) concentrations in dotted or rounded forms, or some other configuration. Preferably, the layers are concentrated or enlarged at the crotch region of the disposable absorbent article.

In one embodiment, the absorbent composite layer of the core has a corrugated configuration. This configuration is characterized by a plurality of pleats (i.e., pronounced fold lines) wherein distinct adjacent sections of the absorbent composite mutually adhere. In another embodiment, the absorbent composite is rolled about a concentration of pulp material such that the pulp concentration is disposed between two layers of the absorbent composite (i.e., "nested"). Further embodiments may utilized a multi-tiered design wherein two or more absorbent composites or two or more absorbent layers are stacked (e.g., at least in the crotch region).

In yet another aspect of the invention, the absorbent composite forms the backsheet and the absorbent core. For example, the nonwoven substrate forms or is provided by the backsheet and the absorbent layer is concentrated at the crotch region to form the absorbent core. Similarly, the absorbent composite may be utilized to form at least a portion of the topsheet and the absorbent core, wherein a section of the topsheet provides the nonwoven substrate of the absorbent composite and the absorbent layer forms the core.

BRIEF DESCRIPTION OF THE DRAWINGS

A better understanding of the invention may be obtained by when a detailed description of the preferred embodiments is considered in conjunction with the appended drawings, in which:

FIG. 5 is a vertical cross sectional view across a core or crotch region of an alternative disposable absorbent article according to the invention;

FIG. 6 is a vertical cross-sectional view of the article in FIG. 5 depicting the article when the absorbent core is wetted or activated;

FIG. 20 is a vertical cross-sectional schematic of a topsheet/absorbent core composite structure employed by an absorbent article according to the invention;

FIG. 21 is a schematic illustration of the construction of a topsheet/absorbent core composite structure employed by an absorbent article according to the invention;

DETAILED DESCRIPTION OF THE DRAWINGS

Upon review of the detailed description and the accompanying drawings provided herein, it will be apparent to one of ordinary skill in the art that the present invention is also applicable to other disposable absorbent articles and more particularly, to disposable absorbent articles such as training pants or other incontinence products. Accordingly, the present invention shall not be limited to the structures and processes specifically described and illustrated herein, although the following description is particularly directed to a disposable diaper. The term "absorbent article" or "absorbent garment" with which the present invention is associated, includes various types of disposable articles and garments which are placed against or in proximity to the body of the wearer so as to absorb and contain various bodily exudates.

Figure 1:
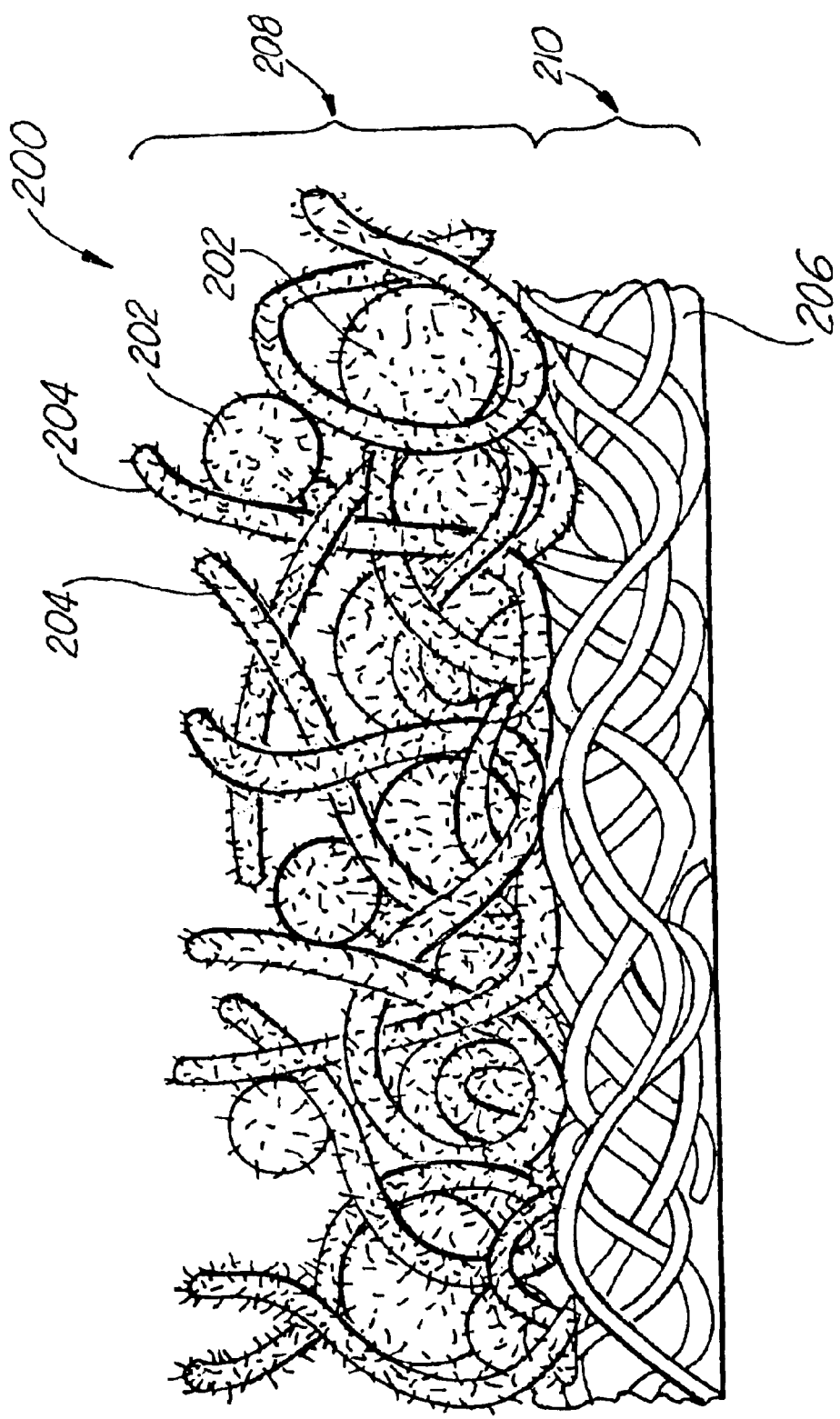
FIG. 1 is a vertical cross-section illustration of a prefabricated absorbent composite employed in the invention.

FIG. 1 depicts (in exaggerated fashion for illustration) an absorbent composite 200 employed in various embodiments of the present invention. The absorbent composite 200 is a prefabricated sheet constructed from water-swellable bodies in the form of super absorbent polymer particles 202 (SAP) which are covered or intermixed with extremely fine micro-fibrillated cellulose 204 (MFC) and embedded into the pores of a low-density nonwoven substrate 206 and anchored thereto (i.e., the MFC acts as a binder). As shown in FIG. 1, the prefabricated absorbent composite 200 includes a low density layer 208 of the SAP and MFC, and a high-density layer 210 of the nonwoven substrate 206. A process of manufacturing a prefabricated sheet of the absorbent composite 200 suitable for the present invention has been developed by the Japan Absorbent Technology Institute (JATI), and is available therefrom under the trade name MEGATHIN. The details of the manufacturing process and other characteristics of the MEGATHIN sheet are described in a PCT international application filed by JATI and issued Reference No. PCT/JP97/04606. The disclosure provided in this and related applications by JATI are hereby incorporated by reference.

In summary, a suitable method of making the absorbent composite (as disclosed in JATI's PCT application) involves dispersing water swellable solid bodies (i.e., the SAP particles) and the hydratable fibers of MFC in a dispersing medium of organic solvent and water. The organic solvent is selected such that it is capable of controlling the swelling of the SAP and dispersing the hydratable fibers and, thus, being miscible with water. The method further involves separating the SAP and fibers from the resultant dispersion liquid in the dispersing medium (e.g, forming a layer of a resultant slurry and spreading the slurry layer over a supporting sheet). Then, the dispersing medium is removed (e.g, from the slurry layer) and the remaining composite dried.

In one aspect of the invention, the invention provides various adaptations of the absorbent composite manufactured, at least partially, by the above-described process. In another aspect of the invention, a plurality of absorbent composites having an array of properties are obtained for implementation in a disposable absorbent article and as various components of the inventive article, including as components of the backsheet, topsheet, absorbent core, containment walls or cuffs (including leg gathers), backsheet/absorbent core composite, topsheet/absorbent composite, and other combinations of these elements.

In one aspect of the invention, multiple functions or advantageous properties are obtained in a single prefabricated absorbent composite sheet structure (suitable for a specific disposable absorbent article design) by varying the basis weight of the SAP and/or the nonwoven substrate, varying the compositions of the low density layer and the nonwoven substrate, varying the detailed construction of the components such as, for example, the degree of SAP cross-linking, and/or applying the absorbent composite at various locations in the article or integrating same with various elements of the article. Specific examples of these variations are provided in more detail in the description of the individual components of the inventive article.

Generally, a higher or faster absorption rate for the SAP (and thus, for the absorbent composite sheet) is achieved by providing an SAP structure with a lower degree of cross-linking construction, whereas a lower or slower absorption rate is achieved by providing an SAP structure with a higher degree of cross-linking construction. The degree of cross-linking (both internally and at the surface of the SAP structure) affects the gross absorbent properties of the SAP including gel strength and AUL (absorbency under load measured at the standard 0.28 psi). It is contemplated that the optimal degree of cross-linking and SAP absorption rate for a particular disposable absorbent article may be obtained through trial and error and after considering other desirable, interdependent properties of the article. In any event, the degree of cross-linking may be selected by examining the free swell capacities of the SAP structure, as well as observing the gel strength, AUL and other gross absorbent properties of the structure. Generally, for purposes of description, high cross-linked SAP have free swell capacities of about 20 to 40 g/g SAP and low cross-linked SAP have free swell capacities greater than about 40 g/g. SAP materials which are typically employed in presently available absorbent products may be considered high cross-linked SAP materials and thus, can be used as a reference. It should also be noted that typical SAP granules employed in these products will have a greater degree of cross-linking at the surface than internally (below the surface), thereby producing a material with a hard coating or surface but which is soft and more absorbent on the inside). For example, one available SAP sheet (polyaspartic acid) is characterized by 0.1 to 30% cross-linking (which is generally high) at the surface and 0.1% to 3.0% internally (which is generally low). See, e.g., U.S. Pat. No. 5,461,085, hereby incorporated by reference.

Below is a more detailed description of compositions (for the absorbent composite) preferred for various embodiments of the inventive disposable article. It should be noted that the SAP components will typically account for over 70% of the absorbent composite.

(1) SAP Surface Linkage Density. Various types of SAP materials are available and primarily distinguishable by their main polymer chains, e.g., by biodegradable or non-biodegradable, salt resistant or non-salt resistant. In many of the embodiments described herein, an acrylic acid super absorbent polymer is preferred. Absorbent properties including absorbent capacity, absorbent speed, gel strength of acrylic acid SAP vary according to the types and concentrations of surface cross-linkage agent. However, it is generally understood to increase the surface cross-linkage density if a high AUL is desired and to decrease the surface cross-linkage density if a high free swell capacity is desired.

(2) SAP Morphology. SAP is available in fiber-state pr particle state including powder state, consolidated particle state, or in needle state. (particle state refers to each of the states except fiber-state). The type of fiber-state SAP preferable in many of the embodiments of the invention will be less than about 10 mm in cut length, but preferably less than 5 mm. Particle state SAP employed in some of the embodiments of the invention will be smaller than about $500\mu$ in particle size but preferably under $400\mu$.

(3) Density of SAP. The density of the SAP employed in several embodiments of the invention will be in the range of about 1.3 to 1.0 $g/cm^2$. If a high absorbent speed is desired, SAP will typically be applied at a density of about 0.3 to 0.5 $g/m^2$. If low absorbent speed is desired, the SAP density will be about 0.6 to 0.9 $g/m^2$. It should be noted, however, that in some applications it will be desirable to apply mixtures of both types (densities) of SAP to achieve a variety of purposes.

(4) Mount volume of SAP. The mount or substrate volume of SAP employed in various embodiments will vary according to the particular application, and more specifically, where it is applied in the diaper. Generally, the SAP mount volume will be the following:

| | |
|---|---|
| Absorbent Core: | 150–500 $g/m^2$ |
| Back Sheet: | 20–500 $g/m^2$ |
| Back Sheet/Absorbent Core Composite: | 50–500 $g/m^2$ |
| Top Sheet/Absorbent Core Composite: | 50–500 $g/m^2$ |
| Containment Walls: | 20–100 $g/m^2$ |

(5) Nonwoven substrate. From many of the embodiments described herein, the nonwoven substrate onto which the SAP layer is applied, is preferably spunbond and SMS (spunbond/meltblown/spunbond)(S1/M/S2)(although S1/M/M/S2 may be preferred in some embodiments). Preferably, different types of spunbond form the upper (S1) and lower (S2) layers. Generally, S1 should be a coarse denier and have a fluffy structure of spunbond. S2 (which may be provided as a supporting layer) should be a fine denier and have a dense structure of paper like spunbond. A middle layer of meltblown should have a structure which would adhere on both sides.

For a backsheet application, it is desirable to have a water resistance of over 200 mm/Aq of at least 200 mm/Aq but preferably about 400 mm/AQ, such that the SMS (whose ratio is between the M layer and the S2 layer) is high. The total basis weight of the SMS is preferably in the range of about 20 to 45 $g/m^2$ and its three components is preferably included in the following: 5~15 $g/m^2$ S1; 5~10 $g/m^2$ M; and 10~20 $g/m^2$ S2.

(7) Absorbent core and topsheet/absorbent core composites. For these composites, a high concentration ratio of S1 is preferable so that a large amount of SAP may be mounted, but should have a lower concentration or ratio of M and S2. For example, the following ratios or concentrations will be preferred in many of the embodiments of this composite: 10~15 $g/m^2$ S1; 0~5 $g/m^2$ M (note that if the concentration of M is 0, the composite is composed only of spunbond); and 5~10 $g/m^2$ S2.

(8) Containment wall and containment wall/absorbent core composite. Since the containment wall should be water-resistant (such as the backsheet), similar compositions will be applied in this embodiment. However, the containment walls are generally thinner than the backsheet but will preferably have a high ratio between M and S2. The following is one composition suitable for this embodiment of the invention: 4~5 $g/m^2$ S1; 5~7 $g/m^2$ M; and 5~7 $g/m^2$ S2.

Generally, the prefabricated absorbent composite sheet 200 employed in the various embodiments of the invention is characterized by a higher SAP content than is conventional, super absorbency, ultra lightweightness, thinness, compactness and stable absorbency due to the microfibril.

Figure 2:
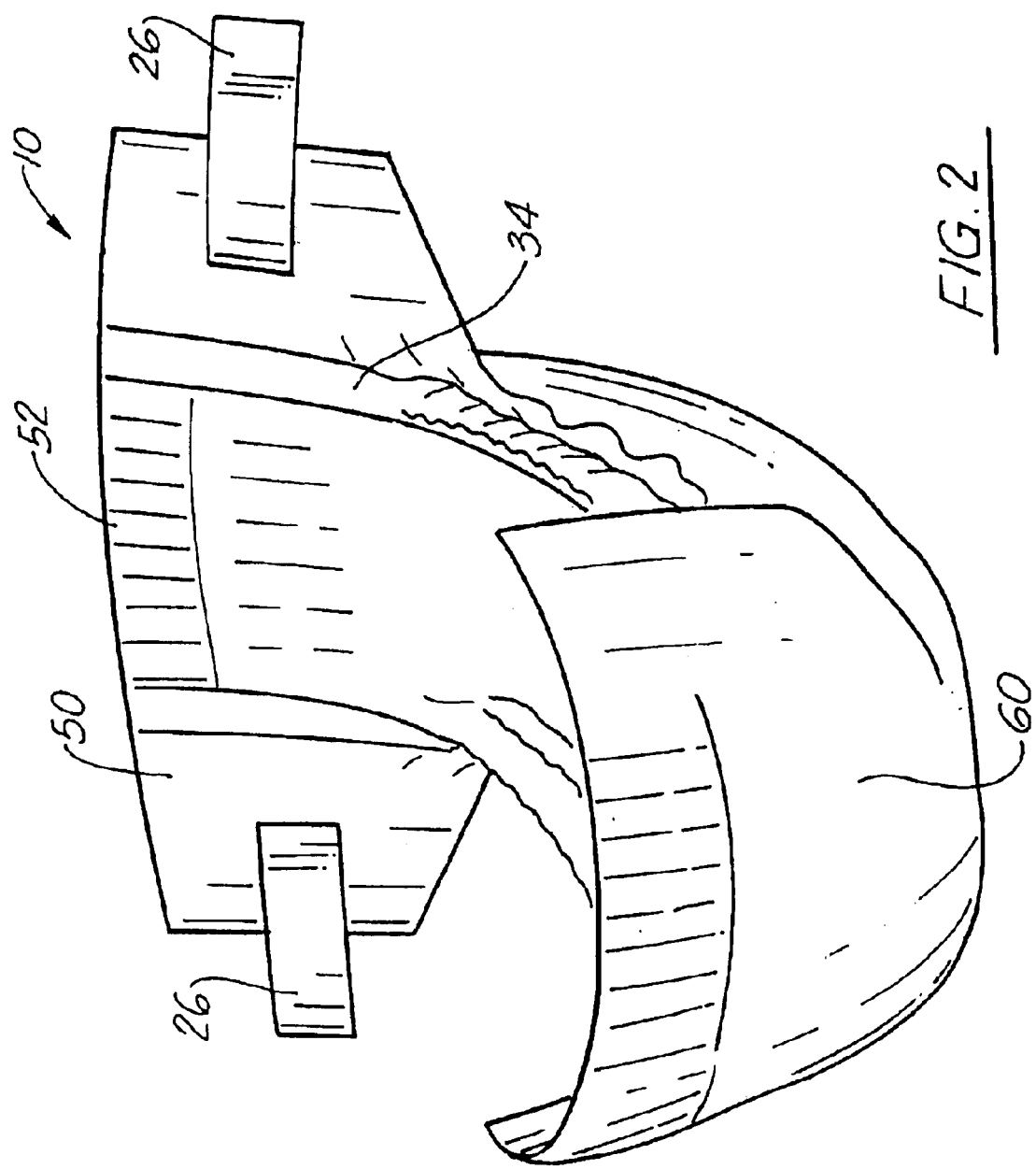
FIG. 2 is a perspective view of a disposable absorbent article embodying the invention.
Figure 3:
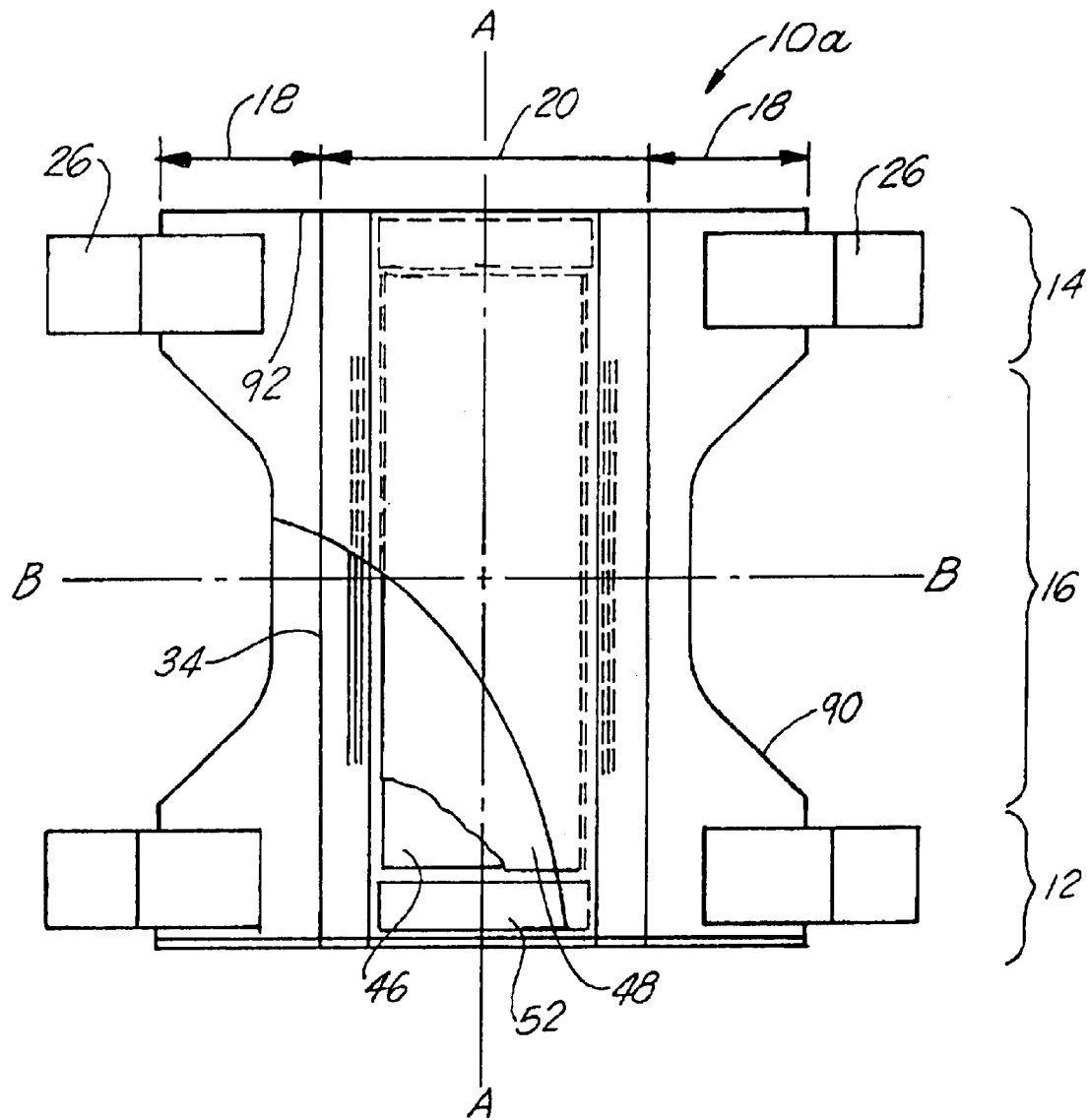
FIG. 3 is a top plan view of the disposable absorbent article of FIG. 2 in a flat and extended condition.

FIG. 2 is a perspective view of a disposable absorbent article 10 in the form of a diaper 10. FIG. 3 illustrates a composite web structure of the diaper 10 in a generally flat and unfolded configuration which the diaper 10 assumes during one point in the manufacturing process (when it is stretched in the longitudinal direction). As will be explained further below, the web structure may be subsequently trimmed, folded, sealed, welded and/or otherwise manipulated to form a disposable diaper 10 in a finished or final form. To facilitate description of the diaper 10 embodying the invention, the description refers to a longitudinally extending axis AA, a laterally extending central axis BB, a pair of longitudinally extending side edges 90, and a pair of end edges 92 which extend between side edges 90 (see FIG. 3). Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of diaper 10.

As shown in FIG. 3, the diaper 10 is characterized by a generally hourglass shape wherein an intermediate portion of side edges 90 (generally in the area of the crotch region 16) is biased generally upwardly (i.e., to partially form upwardly disposed longitudinal walls 34). When the diaper 10 is worn about the waist, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12. The securing surface may be located on or provided by the interior or exterior surface of the front waist region 12. Alternatively, the fasteners 26 may be located on the ears 18 of the front waist region 12 and made securable to the ears 18 of the back waist region 14.

Figure 4:
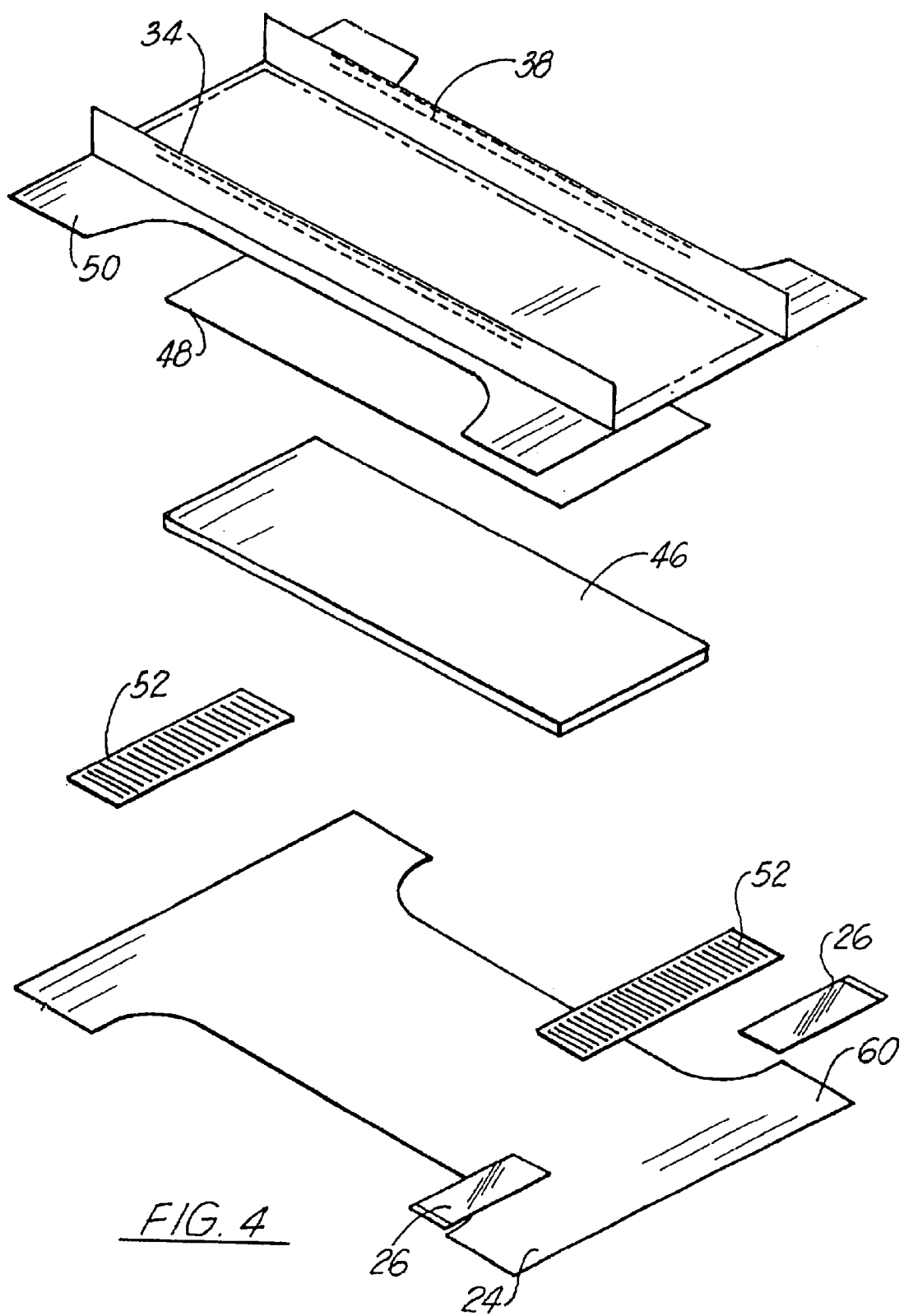
FIG. 4 is an exploded view of the disposable article of FIG. 2.

FIG. 4 is an exploded view of the diaper in FIGS. 2 and 3. A diaper structure suitable for the present invention typically employs at least four layers. These four layers include a backsheet 60, an absorbent core 46, an acquisition layer 48, and a topsheet 50. The diaper structure also includes a pair of containment walls or leg cuffs 34 disposed upwardly from the topsheet 50 and preferably equipped at least with one or more spaced apart, longitudinally elastic members 38. It will be shown below that any of these diaper elements or a combination of these elements may be constructed with or using the prefabricated absorbent composite 200.

Backsheet

The diaper 10 employs a backsheet 60 that covers the core 46 and preferably extends beyond the core 46 toward the side edges 90 and end edges 92 of the diaper 10. In one aspect of the invention, the inventive backsheet 60 is constructed from a single-layered material sheet of a prefabricated absorbent composite 200. As discussed above, such a material sheet includes a low density, absorbent layer 208 of hydratable fine fibers in the form of microfibril 204 obtained from cellulose or a derivative thereof and absorbent polymer particles 202 (SAP) intermixed in and bonded together by the microfibril 204 (see FIG. 1). This absorbent layer 208 is applied as a coating on a nonwoven SMS substrate 206. Preferably, fine particles (e.g., <100 mm) of a soft, low cross-link (i.e., fast absorbent rate) or low gel strength SAP is provided, such that the SAP is adapted to gel block on the nonwoven substrate upon wetting (see earlier discussion). The nonwoven substrate side of the composite sheet 200 is positioned as an outer surface of the backsheet 60, while the SAP side of the sheet 200 is positioned as an inner surface of the backsheet 60 and faces the absorbent core 46. The nonwoven substrate 206 may be provided with printed graphics as is known in the art.

To render a backsheet impermeable according to the invention, various inter-dependent variable or properties may be considered. A lower gel strength SAP (e.g., provided by lower cross-linking or other construction practices) causes the gel particles (i.e., the swollen, wetted SAP particles) to "fit together" thereby preventing leakage of these particles through the "joints" of the sheet structure. It should be noted, however, that too low of a gel strength can cause the gel particles to ooze out of the sheet under pressure (and, thereafter, allow liquid to pass through the sheet). Alternatively, a higher AUL SAP will cause swelling gel particles to press against one another and resist passing of liquid therethrough.

Additionally, the size of pores in the substrate, the basis weight of the SAP and of the substrate, and higher free swell SAP (which correlates with cross-linking) will affect the permeability/impermeability of the inventive backsheet. The net inventive result is a backsheet which, upon activation, exhibits a useful rising column strike through (RCST) without leaking. An RCST value as low as about 2 inches may be adequate for the inventive disposable article, although values closer to about 36 inches will probably ensure prevention of blotting through (i.e., when the wearer sits down on the article) and therefore, are more preferable.

Accordingly, a backsheet of the inventive disposable absorbent article is relatively thin and provides improved flexibility. When dry, the backsheet is soft and breathable, but upon wetting, a thin, gel blocked layer is formed (i.e., on the inner surface of the backsheet) which renders the backsheet substantially liquid impervious.

In yet another aspect of the invention, the thin, liquid impervious gel layer is formed (upon wetting) between the absorbent core 46 and the nonwoven material, thereby eliminating the need of a traditional, poly-film layer under the core (e.g, on the backsheet at the crotch region). However, unlike the prior art disposable absorbent article that employs a poly-film layer, that area of the inventive article is normally breathable (i.e., when wet) and more flexible and comfortable. Moreover, due to the elimination of the poly-film layer, a thinner, simpler diaper structure is produced.

The absorbent composite 200 for the backsheet 60 in the Figures preferably employs SAP in a concentration of about 20 $g/m^2$ to 100 $g/m^2$ suspended in MFC. The absorbent composite 200 also employs a nonwoven layer of spun bond/melt blown/spun bond (SMS) having a total basis weight of about 20 to 45 $g/m^2$.

Topsheet

When the diaper 10 is worn, the topsheet 50 is placed in close proximity to the skin of the wearer. The topsheet 50 is preferably soft, compliant, exhibits good strikethrough and a reduced tendency to rewet from a liquid pervious material. In this way, such a topsheet 50 permits bodily discharges to rapidly penetrate it so as to flow toward the core 46 more quickly, but not allowing such discharges to flow back through the topsheet 50. The topsheet 50 may be constructed from any one of a wide range of liquid and vapor permeable hydrophilic materials. The topsheet 50 may consist of or include nonwoven webs of natural fibers (e.g., wood or cotton) or synthetic fibers (e.g., polypropylene or polyester), or a combination of such webs or fibers, or apertured film.

One topsheet material suitable for the inventive garment is a 15 $g/m^2$ spun bond polypropylene available from Avgol nonwovens of Holon, Israel. The surface (s) of the topsheet may be treated with a surfactant so as to facilitate liquid transfer therethrough, especially at a central zone or area of the topsheet located over the core and an inner surface of the core. The topsheet may also be coated with a substance having rash preventing or rash reducing properties (e.g., aloe vera).

In one embodiment, the topsheet 50 is formed from a single-layered material sheet that covers substantially the entire area of the disposal absorbent article 10, including substantially all of the front waist region 12, back waist region 14, and cross regions 16. Further, the ear layer of the inner region 18 is formed from the same single topsheet material and, thus, may be referred to as being unitary with the topsheet 50 in forming lateral extensions of the topsheet material. Alternatively, the topsheet 50 may be formed from multiple different materials which vary across the width of the topsheet 50 such a multiple piece design allows for creation of preferred properties and different zones of the topsheet.

Referring now to FIG. 5, in one particular embodiment of the invention, the topsheet 50 is raised or spaced, at least partially, above the core 46 by a plurality of longitudinally extending elastic strands 102. The strands 102 form spaced apart ridges 152 on the topsheet 50 in valleys or depressions 154 between the ridges 152. The valleys 154 are tacked down to the core 46 at bond points 106 or to the acquisition layer (not shown). Such a "tented" topsheet 50 directs liquid received therein into the valleys or depressions 154. As will be further explained below, the core 46 according to the invention is preferably constructed from the prefabricated absorbent composite 200. The core 46 is designed to absorb liquid received below the topsheet 50 and to swell upon wetting such that the SAP fill the zones or voids under the topsheet 50 (see FIG. 6). The swelling SAP also further reinforces the three-dimensional tented structure. Preferably, the core 46 is comprised of a plurality of longitudinally-extending, laterally spaced-apart core segments (see description of core structures below) each of which are disposed under the "tented" topsheet (i.e., in the void areas). Alternatively, the core 46 may be a single sheet structure having distinctly higher SAP concentrations in the void areas than along the bond points (see FIGS. 6 and 7). Variations of this type of core design, each of which is suitable for the "tented" topsheet configuration, are discussed further below.

In any one of the embodiments of inventive disposable absorbent article, the SAP absorbent layer may be coated with a miscible, hydrophobic material. The coating acts as a barrier or membrane that initially slows the liquid uptake, thereby saving SAP capacity for additional or secondary discharges. In this regard, the coating evens out the absorbency rates between discharges. The coating may take the form of any type of miscible, hydrophobic material film or membrane.

In one embodiment, a light coating of mineral oil is applied over the SAP absorbent layer (e.g., over the surface of the SAP granules). The coating retards the initial uptake of the SAP and allows more time for the liquid to spread out in the article. Preferably, the mineral oil is applied at a concentration of about 0.11 g/g of SAP to about 1.0 g/g of SAP (depending on the particular product design). Alternatively, the mineral oil may be applied in specific target zones. In this way, the received liquid is encouraged to initially spread to uncoated areas before the coated areas are activated and begin to swell.

In one embodiment, the prefabricated absorbent composite 200 includes a topsheet layer (e.g., over the low density layer 206). The prefabricated absorbent composite 200 is disposed in the crotch region of the disposable absorbent article (i.e., over the backsheet and provides both the topsheet and core (i.e., in one material sheet) for the article. The topsheet or a section thereof may also provide the nonwoven substrate 206 for the absorbent composite 200.

Absorbent Core

An absorbent core 46 employed by the disposable absorbent article 10 according to the invention is preferably constructed with the prefabricated absorbent composite 200 (previously discussed). More particularly, such an absorbent composite 200 for the core 46 typically consists of a relatively high loft, nonwoven material coated with a super absorbent polymer structure. A core according to the invention is therefore, nearly as thin as a typical nonwoven substrate raw material, but has an SAP basis weight found in a regular diaper core. FIGS. 7–12 depict various embodiments of the invention, wherein the above described absorbent composite 20 is utilized as the primary or unitary element of the core structure, and wherein like elements are identified by like reference numerals. As shown in these drawings, the inventive core 46 may employ a uniform layer of the absorbent composite 200, a non-uniform structure layer in which the low density SAP layer is applied in a segmented layer or in, otherwise, distinct space-apart zone layers, in multi-tiered layers, or in other variations.

Figure 8:
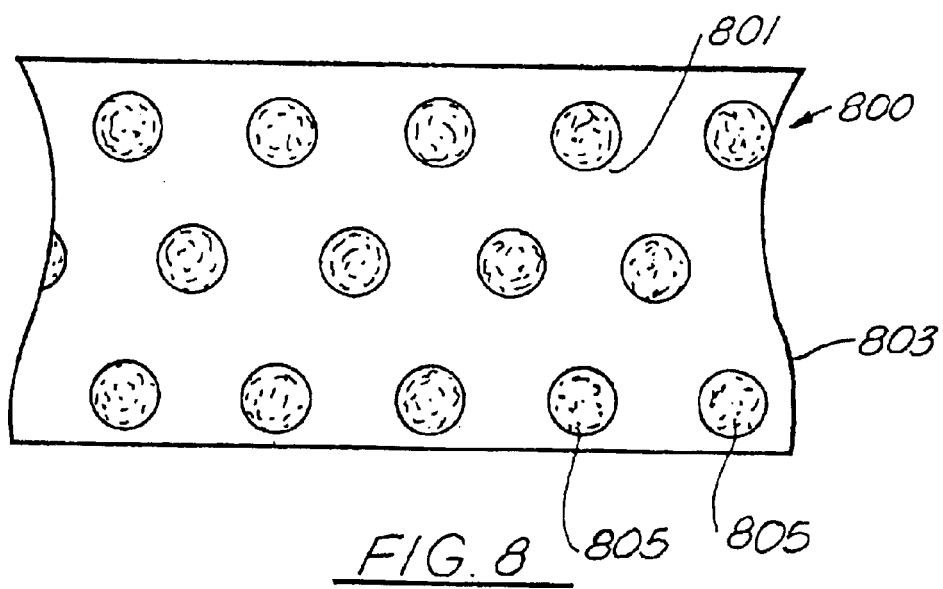
FIG. 8 is a plan view illustration of an absorbent core employed by an alternative absorbent article according to the present invention.
Figure 7:
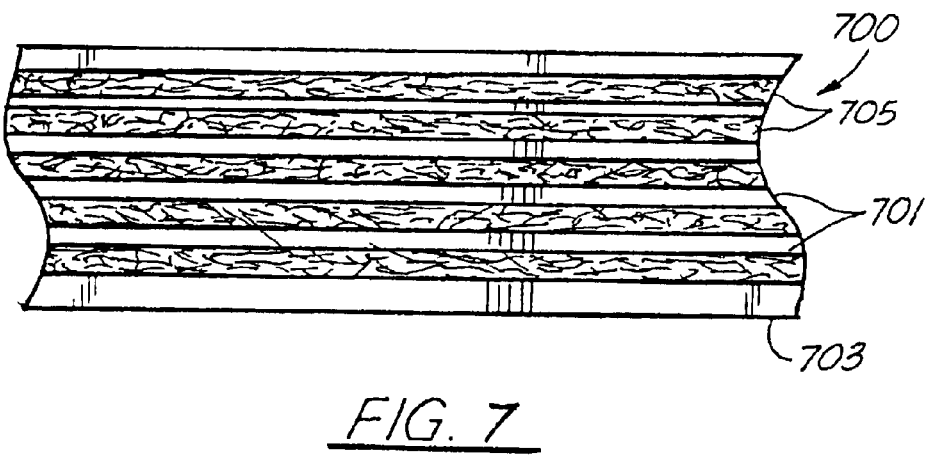
FIG. 7 is a plan view illustration of an absorbent core employed by an absorbent article according to the present invention.
Figure 9:
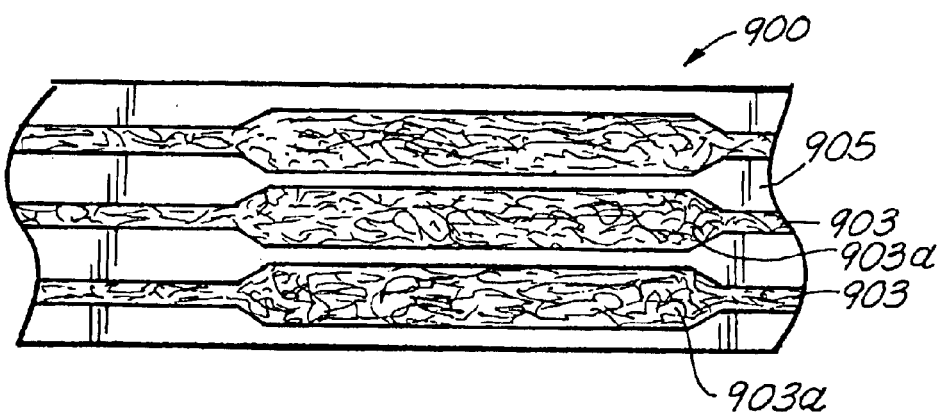
FIG. 9 is a plan view illustration of an absorbent core employed by another alternative absorbent article according to the invention.

Each of FIGS. 7–9 depicts a continuous sheet 700,800, 900 (including a core structure) constructed of a prefabricated absorbent composite having a plurality of distinct, spaced-apart or segmented SAP concentrations or layers deposited on a nonwoven substrate.

The plan view of FIG. 7 depicts a composite structure 700 (and prefabricated absorbent composite) in which the low-density SAP layers or concentrations (with MFC) is applied over a nonwoven substrate 703 in longitudinally-extending segments. Such a design provides uncoated bands or zones 701 between the SAP segments 705. The wicking zones 101 are particularly adapted to wicking (i.e., wicking zones 701) and allow the SAP segments 700 freedom to expand or wick in the lateral directions without gel blocking. In this manner, the absorbent capacity of the SAP is maximized or fully utilized. More specifically, this segmented design ensures that the SAP layer will be fully wetted out and also reduces pressure between the SAP particles (thereby allowing liquid to flow therebetween and promoting complete saturation). Preferably, the width of the core segments 705 is in the range of about 1–15 mm, and the wicking zones have a width in the range of about 1–25 mm.

In the embodiment depicted in the plan view of FIG. 8, the composite structure 800 (or prefabricated absorbent composite) includes a nonwoven substrate layer 803 onto which distinct, spaced-apart SAP concentrations or SAP layers 805 are applied. The SAP concentrations are formed by distinct dotted or rounded layers 805 of the high-density SAP material and MFC. Similar to the longitudinally-extending segmented layer design of FIG. 7, the spaces between the dots 805 are uncoated wicking zones 801 which allow the SAP dots 805 freedom to expand or wick in all directions without gel blocking. Again, such a design allows full utilization of the absorbent capacity of the SAP by ensuring complete wetting and reducing the pressure between the SAP particles. Preferably, the SAP dots 805 will have diameters in the range of about 2 to 20 mm, and are spaced from one another by an average distance of about 1 mm to 10 mm. Also, the arrangement of the SAP dots 805 is preferably a staggered pattern as shown in FIG. 8, such that the areas of the wicking zones 801 are generally uniform and equally maximized.

FIG. 9 depicts yet another composite structure 900 embodying a variation of the segmented absorbent core according to the invention. The spaced-apart segmented SAP layers 903 each has a high SAP concentration section 903a and are applied onto a nonwoven substrate 905. In one respect, such a design may be described as providing high concentration SAP target areas, wherein the core exhibits higher absorbent capacity due to the higher SAP concentration. For example, in FIG. 9, the high concentration or wider SAP sections 903 will be strategically positioned in the central crotch region. It should be noted that such target areas may utilize not only segmented SAP layers of various shapes and sizes, but also uniform, multi-layered or multi-tiered layer designs as well (see e.g., FIGS. 10–12).

Figure 10:
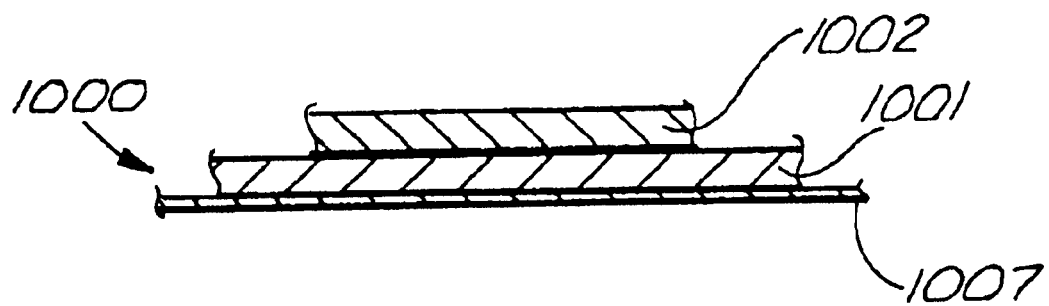
FIG. 10 is a vertical cross-sectional view schematic of an alternative absorbent article according to the invention.

FIG. 10 depicts yet another composite structure 1000 embodying a variation of the inventive core wherein a high SAP concentration is provided in the central crotch region 16. The absorbent core 46 employs a multi-tiered absorbent composite structure, and more specifically, a smaller secondary absorbent composite layer 1002 applied over the larger first absorbent composite layer 1001. In further embodiments, the secondary absorbent composite layer 1002 may be replaced with high concentrations of spaced-apart, longitudinally-extending segmented layers, dotted layers, and the like, so as to achieve higher absorbent capacity in the target area, i.e., crotch region. The composite structure 1000 in FIG. 10 also utilizes a bottom or substrate layer 1007, e.g., a backsheet.

Figure 11:
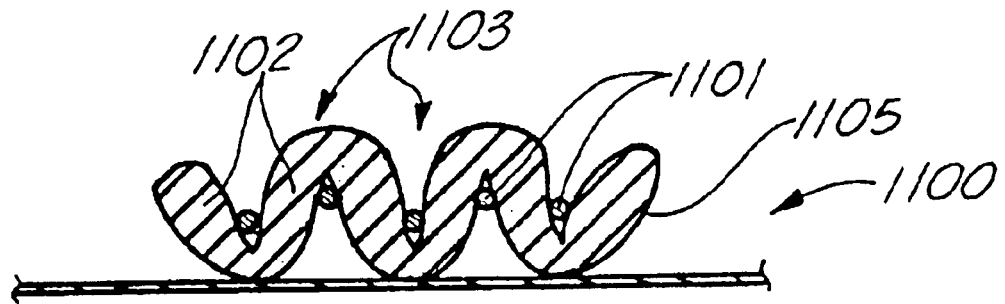
FIG. 11 is a vertical cross-sectional view schematic of an alternative absorbent core employed by an absorbent article according to the invention.

The vertical cross-sectional view of FIG. 11 depicts yet another composite structure 1100 embodying a variation of an absorbent core according to the invention, and which employs a prefabricated absorbent composite disposed in a corrugated configuration. As shown therein, an absorbent composite 1105 is folded into multiple "V" structures 1103 made up of two folds or sections 1102 having flexible gaps therebetween. The folds 1102 are glued together at bond points 1101 so as to keep the pleated layers or "V" structures 1103 attached to one another. Such a corrugated structure serves the auxiliary function of increasing the surface area of the absorbent composite, thereby increasing the speed of liquid flow into the absorbent materials and increasing the absorbent capacity of the core. In a relatively wide diaper in the prior art, when the diaper is worn, the absorbent core folds into a "V" between the wearer's legs, and the absorbent materials of the core are held some distance away from the wearer. In the corrugated core design of FIG. 11, the multiple small "V" folds 1103 hold the core closer to the wearer than one single, large "V" fold. In this manner, a relatively narrow core is produced which moves dynamically with the wearer, rather than move away from the wearer (as in the prior art).

Figure 12:
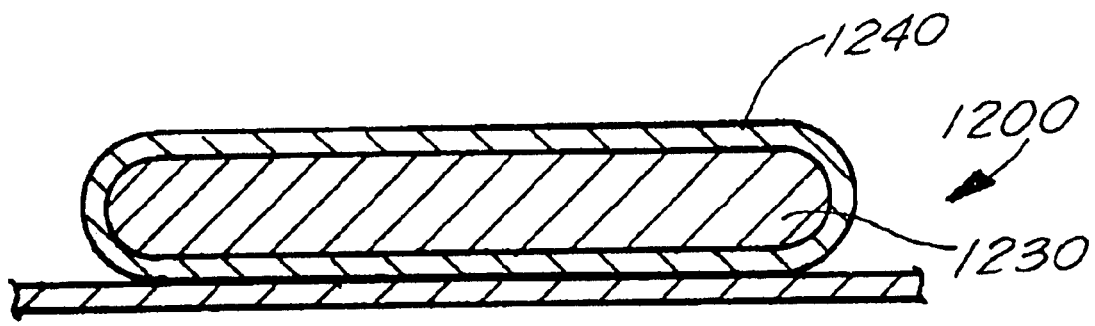
FIG. 12 is a vertical cross-sectional view schematic of an alternative absorbent core employed by an absorbent article according to the invention.

FIG. 12 depicts yet another composite structure 1200 embodiment of the inventive disposable absorbent article according to the invention. In this embodiment, the article employs an absorbent composite structure 1200 as an absorbent core 1200 configured in a nested doll structure. The nested doll core, includes a prefabricated sheet of absorbent composite 1240 that is rolled substantially about a pulp concentration 1230. The pulp concentration 1230 provides wicking and facilitates liquid distribution, while the prefabricated absorbent sheet 1240 provides structural integrity. It should be understood that the absorbent layer 1240 may employ multiple sheets or layered configurations as discussed before. For example, the uniform sheet layer in FIG. 12 may be replaced with or supplemented by segmented layers of SAP concentrations similar to those shown in FIGS. 7–9.

Moreover, the core according to various embodiments of the invention may be configured to extend substantially the full length and/or width of the disposable absorbent article. Preferably, however, the core is disposed or is otherwise concentrated at the crotch region of the article. In various embodiments, the core includes a sheet or layer that extends to the edges of the article and an absorbent composite(s) is concentrated in the crotch region or another target zone of the article.

The core may also include additives which provide specific properties for the article. For example, baking soda may be added to provide improved odor absorbency. Further, a nonwoven sheet may be added to provide added flexibility and stretchability.

Backsheet/Absorbent Core Composite

Figure 17:
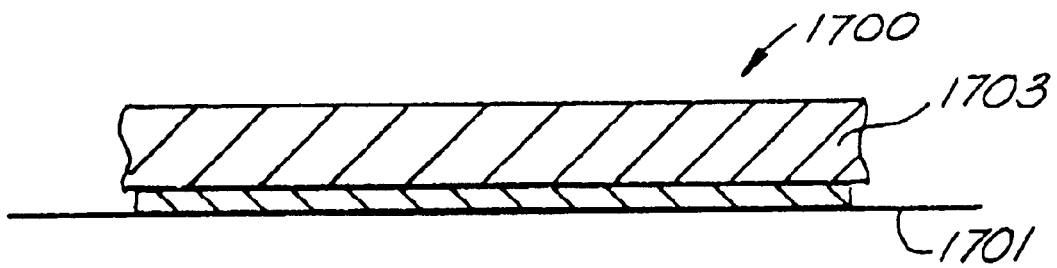
FIG. 17 is a vertical cross-sectional view schematic of a backsheet/absorbent core composite employed by an absorbent article according to the invention.
Figure 18:
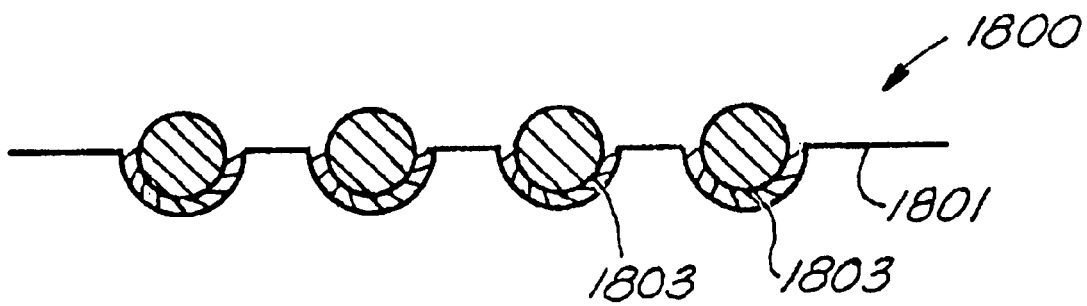
FIG. 18 is a vertical cross-sectional view schematic of an alternative backsheet/absorbent core composite employed by an absorbent article according to the invention.
Figure 19:
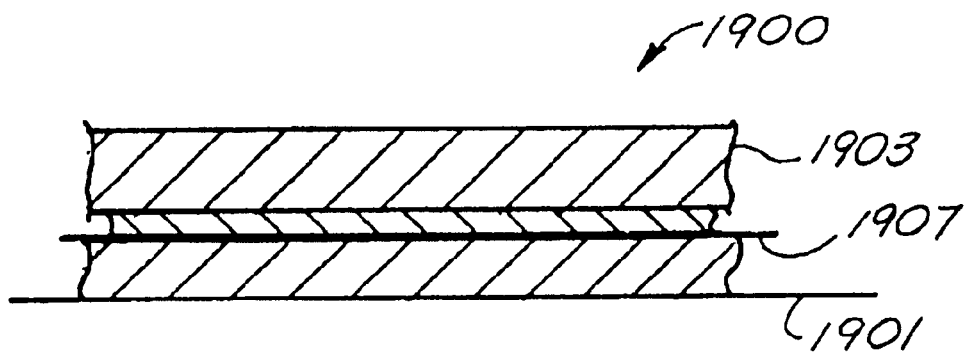
FIG. 19 is a vertical cross-sectional view schematic of an alternative backsheet/absorbent core composite employed by an absorbent article according to the invention.

Each of FIGS. 17–19 depicts a backsheet/absorbent core composite 1700, 1800, 1900 utilizing the prefabricated absorbent composite sheet 200. In these embodiments, the backsheet and absorbent core composite 1700, 1800, 1900 replaces the traditional backsheet-poly-film barrier-absorbent core assembly in the prior art. Referring to FIG. 17, the backsheet 1701 is formed by an SMMS and SMS liquid barrier layer combination 1701 that extends beyond the crotch region of the article 10 and preferably to the edges of the article 10. In the crotch region 16 of the article 10, an absorbent composite of the SMS nonwoven substrate 1701 and a low-density, high SAP content absorbent layer 1703 together (i.e., applied by hot melt adhesion over the substrate 1701) forms the absorbent core. In FIGS. 17 and 19, the crotch region 16 of the article 10 is provided with a single, uniform layer of the absorbent composite 1700, 1900 including an absorbent layer 1703, 1833 preferably having an SAP content about 180 g/m². In the composite 1900 of FIG. 19, a second SMS and SMMS combination layer 1907 is added (e.g., by hot melt) to the composite for extra leakage protection.

In FIG. 18, a plurality of segmented, elongated high SAP content (e.g., about 120 g/m²) absorbent composite layers 1803 are provided in the crotch region 16 to form the core. Preferably, the SMMS backsheet layer 1801 forms about the rounded contour of the absorbent composites or cores 1803, thereby creating pockets or channels in which the absorbent composites 1803 are disposed.

Each of FIGS. 20 and 21 depict a topsheet/absorbent core composite structure that may be utilized in a disposable absorbent article 10 according to the invention. These designs eliminate the need for the traditional three component design of a topsheet, acquisition layer and absorbent core structure, and provides instead a single layer of topsheet and absorbent core composite. In a first embodiment illustrated in FIG. 20, the absorbent composite 2000 includes a two-layer nonwoven with an SAP coating. The two-layer nonwoven is preferably provided in a concentration of about 35 g/m², while the SAP is preferably provided in a concentration of about 150 g/m².

The two-layer nonwoven consists of a fine PE/PET bicomponent fiber layer 2003 and an PET/Rayon layer 2001. The PE/PET bicomponent is preferably at about 1.5 denier, thermobonded, and has a basis weight of about 10 g/m². The PET/Rayon layer 2001 is preferably 50% PET and 50% Rayon, wherein the PET is at about 5 denier and the Rayon is at about 1.5 denier. Together, the PET/Rayon mixture is preferably in a concentration of about 25 g/m². As shown in FIG. 20, the two-layer nonwoven is preferably immersed in an SAP slurry coating to produce the composite 2000. Note that the SAP particles 2005 are positioned below the PE/PET and on the underside of the composite, thereby providing the absorbent core of the disposable absorbent article 10 of the invention.

FIG. 21 illustrates a second embodiment of a topsheet/absorbent core composite structure that may be utilized in an inventive disposable absorbent article 10. FIG. 21 also illustrates the components which make up the composite structure and how such components are combined to produce the composite structure. Generally, the composite structure 2100 includes a nonwoven layer 2102 that is preferably a thermal bonded PE/PET bicomponent at 3 denier and a basis weight of 40 g/m². The SAP slurry (which provides the SAP) is preferably at a concentration of about 150 g/m² and is coated in a segmented fashion (to the nonwoven layer 2106) to form a plurality of absorbent layers 2104. Then, the absorbent composite 2100 may be folded between the absorbent layer segments 2104 and elastic elements 2106 added so as to form a tented structure. Elastic elements 2106 are preferably provided underneath the topsheet at a location corresponding to the peaks thereof. The absorbent composite 2100 is preferably fixed to the backsheet 2108 by, for example, hot melt adhesion. It should be apparent that this tented structure employing the absorbent composite structure 2100 provides a relatively thin absorption area, but one having an increased surface area.

Containment Walls

Figure 13:
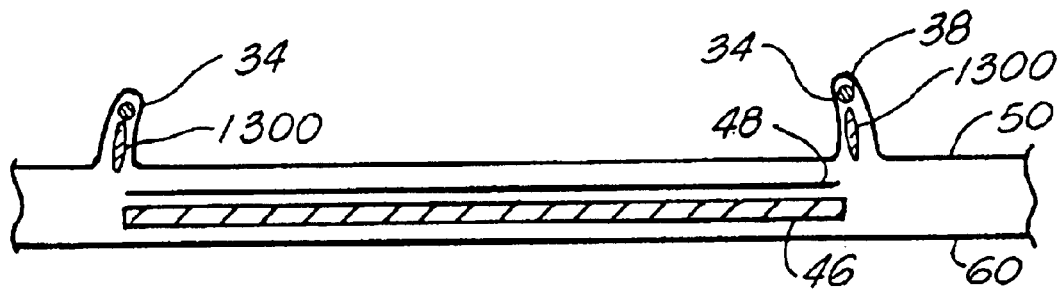
FIG. 13 is a vertical cross-sectional view schematic of an alternative embodiment of a disposable absorbent article according to the invention.
Figure 14:
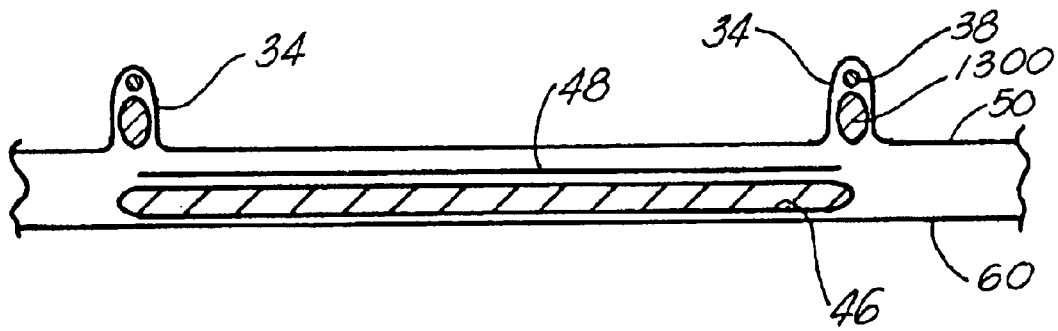
FIG. 14 is a vertical cross-sectional view schematic of the disposable absorbent article of FIG. 13 depicted in the "wet" condition.

Now turning to FIGS. 13 and 14, in yet another aspect of the invention, the inventive disposable absorbent article 10 utilizes a pair of containment walls or cuffs 34 which employ a prefabricated absorbent composite 200. Each containment wall 34 is a longitudinally extending wall structure preferably positioned on each side of the core 46 and spaced laterally from the longitudinal center. The longitudinal ends of the walls 34 may be attached, for example, to the topsheet 50 in the front and rear waist regions 12, 14. Preferably, the ends of the containment wall 34 are tacked down inwardly and attached, for example, by adhesive to the web structure 10a. Such a construction effectively biases the containment wall 34 inwardly and is generally considered to cause containment wall 34 to exhibit improved leakage prevention properties.

FIG. 13 provides a vertical cross-sectional view of a diaper 10 according to the invention. The diaper 10 includes backsheet 60, absorbent core 46, acquisition layer 48, and topsheet 50. The diaper 10 also includes a pair of containment walls or cuffs 34 which are formed by folding topsheet 50 and wrapping it about a prefabricated absorbent composite 1300. The width of the absorbent composite 1300 may generally equal the height of the containment walls 34, while the length of the absorbent composite sheet 1300 may extend the full length of diaper 10 (or at least through the crotch region 16). Furthermore, the containment walls 34 may be biased inwardly toward the center.

Preferably, the containment walls 34 are equipped with elastic members 38, which extend along a substantial length of the containment walls 34. In a common application, the elastic members 38 are placed within the containment walls 34, preferably at the top of the containment walls 34 while in a stretched condition and then glued to the containment walls at least at their ends. When released or otherwise allowed relaxing, the elastic members 38 retract inwardly. When the article 10 is worn, the elastic members 38 function to contract the containment walls 34 about the buttocks and the thighs of the user in a manner, which effects a seal between the article 10, the buttocks and the thighs.

FIG. 13 depicts the configuration of the containment walls 34 when it is soft and dry. FIG. 14, on the other hand, depicts the containment walls after wetting, in which the absorbent composite 1300 (i.e, the SAP) has swollen to dispose the containment walls 34 in a resiliently, erect position. Unlike traditional leg cuffs in the prior art, the resiliently erect containment walls 34 resists flattening (e.g., when the wearer sits down) and, thereby, ensures leakage prevention, especially of explosive, liquefied bowel movements and rapid discharges of urine.

In a further embodiment of the invention, the disposable absorbent article may employ multiple containment walls, including inner containment walls which are shorter than outer containment walls (closer to side edges 90).

Figure 15:
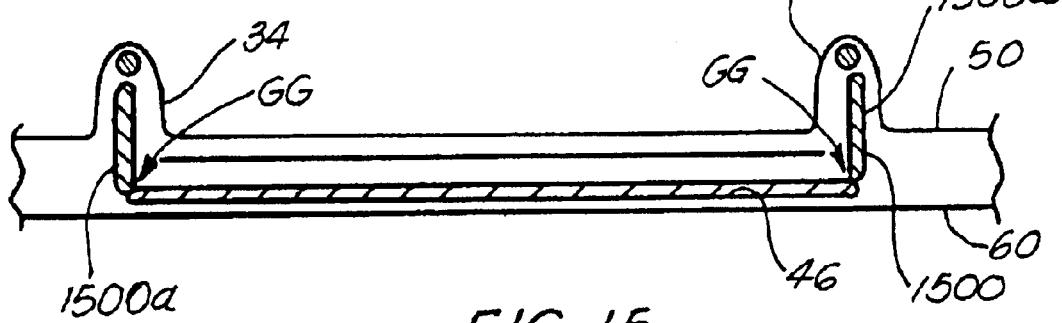
FIG. 15 is a vertical cross-sectional view schematic of an alternative embodiment of a disposable absorbent article according to the present invention.
Figure 16:
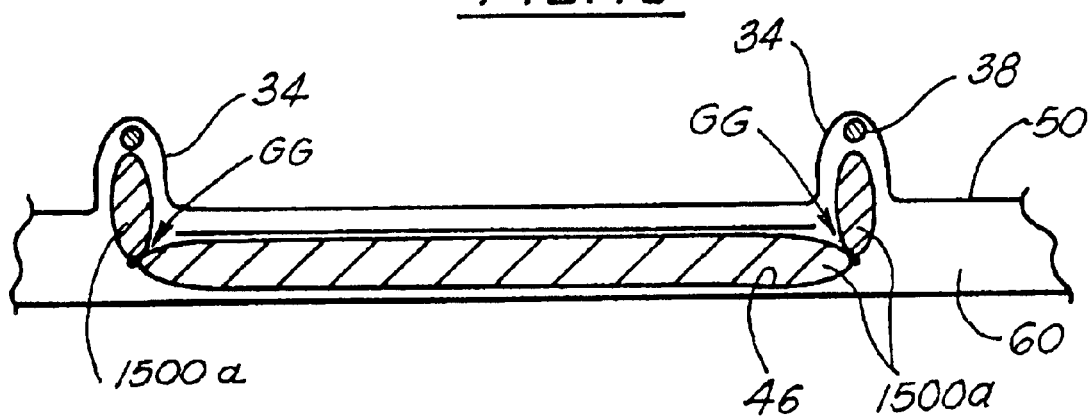
FIG. 16 is a vertical cross-sectional view schematic of the disposable absorbent article of FIG. 15 depicted in the "wet condition;"

FIG. 15 depicts yet another variation of the inventive disposable absorbent article 10. The article 10 includes containment walls 34 and an absorbent core formed from a continuous piece of prefabricated absorbent composite 1500. The absorbent composite 1500 includes three SAP sections 1500a with a non-SAP coated band along their intersections (GG). Note that the intersection GG corresponds to the location where the single continuous prefabricated sheet 1500 is folded. As described above, the containment wall 34 which contains the prefabricated absorbent composite sheet 1500, stays soft when dry (FIG. 15), but swells to a resilient erect position when wetted (FIG. 16). Accordingly, the containment walls 34 resist being flattened, like traditional leg cuffs, when the wearer is in the sitting position, thereby helping prevent leakage.

Figure 22:
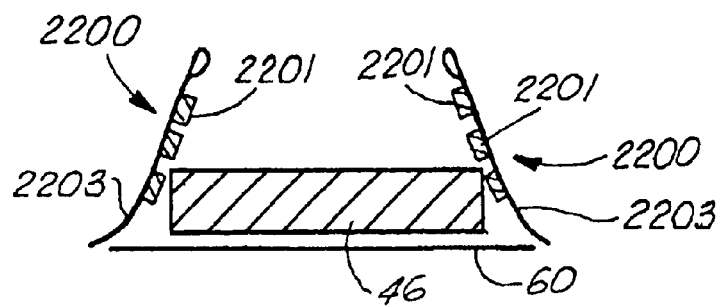
FIG. 22 is a schematic of a vertical cross-sectional view of a containment wall/absorbent core composite structure employed by an absorbent article according to the invention.
Figure 23:
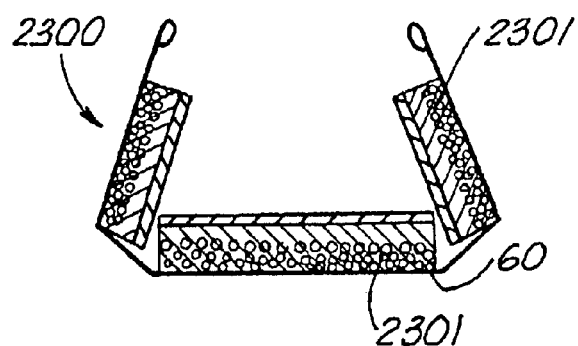
FIG. 23 is a schematic of a vertical cross-sectional view of an alternative containment wall/absorbent core composite structure employed by an absorbent article according to the invention.
Figure 24:
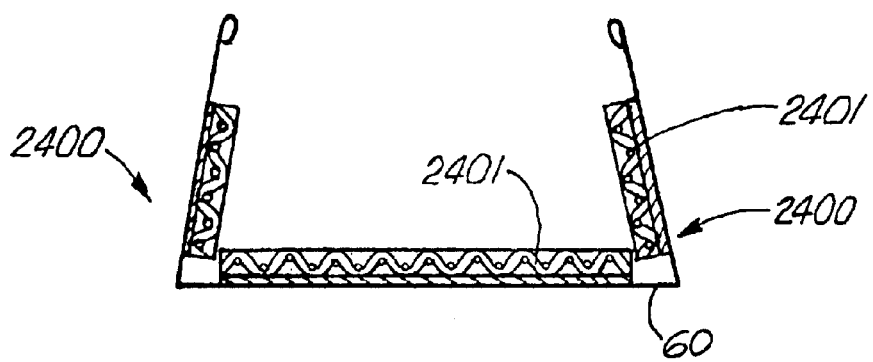
FIG. 24 is an alternative schematic of a vertical cross-sectional view of an alternative containment wall/absorbent core composite structure employed by an absorbent article according to the invention.

Each of FIGS. 22–24 depicts the use of the prefabricated absorbent composite 2200, 2300, 2400 in the construction of the leg gathers (i.e., another type of containment wall) of a disposable absorbent article 10 according to the invention. In FIG. 22, a material sheet of the absorbent composite 2200 is used to form the upstanding containment walls or cuffs, wherein the segmented high SAP content absorbent layers 2201 are disposed inwardly to face the crotch region). Conversely, the nonwoven substrate 2203 is located on the outside or outboard of the crotch region.

FIG. 23 depicts an alternative embodiment of the leg gathers employing an absorbent composite 2300, according to the invention. The absorbent composite employed in this embodiment is similar to that illustrated and described with respect to FIG. 20 (above). Further, in this embodiment, an absorbent composite is also provided (e.g., with the backsheet 60 as to the nonwoven substrate) as the absorbent core of the diaper.

FIG. 24 depicts yet another variation of a use of the absorbent composite 2400 in a disposable absorbent article 10 of the invention. In this embodiment, a conventional backsheet 60 provides the nonwoven substrate for each of the three absorbent composites. The absorbent composites 2400 provides not only the core structure, but an absorbent layer 2401 for each of the cuff structures.

Optional Layers

The disposable absorbent article according to the invention may employ additional layers including an acquisition layer or surge layer, preferably situated between the topsheet and the core (e.g., FIG. 4). One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

The acquisition layer may be constructed from the absorbent composite 200. More specifically, the acquisition layer 48 may be provided by a sheet of the absorbent composite 200 with an SAP having a high gel strength and a high loft substrate. Such an acquisition layer sheet advantageously becomes more porous upon wetting. This property is further improved by providing a high loft nonwoven substrate such as through-air bonded nonwovens or any other standard acquisition layer product. Accordingly, typically, dual layers—an acquisition layer and a distribution layer—are employed in the prior art. However, in the present invention, the acquisition layer is provided by the single sheet acquisition layer constructed from the absorbent composite 200. With the inventive acquisition layer constructed from the absorbent composite 200, very stiff granules within the sheet expand upon wetness and provides pores or passages through the sheet (rather than collapsing).

Tape Tabs

The disposable absorbent article must be secured to the wearer. This is most important with respect to diapers since diapers are not pulled up by the wearer, like training pants or incontinent briefs, but are fastened around the wearer. Securing elements compliment the elastic members by effecting a quasi-seal between the wearer and the waistband and leg cuffs, so that liquid is contained within the article which is then absorbed; in other words, so that it does not leak through gas between the wearer and the edge of the article. The securing elements may be adhesive, mechanical fasteners hook and loop features, or conceivably strings, i.e., anything that will secure one end of the article to the longitudinally opposite end.

In the embodiments shown in the Figures (see, e.g., FIG. 4), the article 10 is affixed to the wearer by tape fasteners 26 which are permanently affixed to (e.g., sewn directly into) the backsheet 60. Tape fasteners 26 are contacted with the transversely opposite ear 22 extending from the backsheet, where they remain affixed due to adhesive compound applied to the fasteners 26.

Waistband

Waistbands employing elastic members are positioned along the transverse portion of the article 10 so that when worn, the waistbands are positioned along the waist of the wearer. Generally, the waistband preferably creates a quasi-seal against the waist (transverse elastic members 52) so that liquid waste does not leak from the regions between the waist elastic and the waist of the wearer. The quasi-seal is significant because although the liquid may be eventually absorbed by filler material, the assault of liquid by the wearer may overwhelm the absorption rate capacity of the filler material. Hence, the waistbands contain the liquid while it is being absorbed. Secondly, the waistbands preferably has a capacity to absorb liquid (see, e.g., U.S. Pat. No. 5,601,544, which is hereby incorporated by reference).

Article's Shape

The shape of the article can provide certain attributes. An article providing a more precise contour around the wearer's crotch area will less likely bunch up. In this way, The article helps to prevent pools of liquid from building up and locally saturating underlying filler material. The article's shape can also be manipulated to control the seal or the closure of gas between the edges of the article and the wearer. A narrower profile may be desirable to achieve a smooth liquid contact zone against the wearer's crotch (i.e., no bunching). However, a narrower profile also means less surface area available for filler material thereby decreasing the article's absorption capacity. Similarly, a larger profile can more readily accommodate a variety of sizes, whereas a narrower profile may not be suitable for larger wearers. However, a larger article may be more costly to manufacture and require a higher ticket price.

The present invention is, therefore, well adapted to carry out the objects and attain the ends and the advantages mentioned, as well as others inherent therein. While presently preferred embodiments (in the form of a diaper) have been described, numerous changes to the details of construction, arrangement of the article's parts or components, and the steps to the processes may be made. For example, the various topsheets, backsheet, absorbent core, containment walls and other absorbent composite structures may be utilized in other parts of the article or with other articles other than diapers. Such changes will readily suggest themselves of those skilled in the art and are encompassed within the spirit of invention and in the scope of the appended claims.

What is claimed is:

1. A disposable absorbent article comprising:
   a topsheet;
   a backsheet; and
   an absorbent core disposed therebetween;
   wherein said absorbent core is constructed of a first absorbent composite including
   an absorbent layer of hydratable fine fibers in the form of microfibril obtained from cellulose or a derivative thereof, and super absorbent polymer (SAP) particles bonded together by said hydratable fibers, a coating of mineral oil over said SAP particles of said absorbent layer, said coating being adapted to retard the initial receipt of liquid by said SAP in said absorbent layer, and
   a nonwoven substrate supporting said absorbent layer, said absorbent layer being coated thereupon; and
   a pair of longitudinally-extending, upstanding cuffs spaced laterally from said core, each said cuff including a folded portion of said topsheet and a longitudinally-extending absorbent composite section secured within said folded portion, said longitudinally-extending absorbent composite section including an absorbent layer of hydratable fine fibers in the form of microfibril obtained from cellulose or a derivative thereof, an super absorbent polymer (SAP) particles bonded together by said hydratable fibers, and a nonwoven substrate supporting said absorbent layer, said absorbent layer being coated thereupon; and
   wherein said first absorbent composite of said core and said longitudinally extending absorbent composite sections of said cuffs are distinct swellable SAP sections of one continuous absorbent composite structure positioned about a crotch region of said article, said continuous absorbent composite structure being folded between each said longitudinally extending absorbent composite section and said absorbent core to form a substantially non-swellable intersection therebetween; and
   wherein said absorbent layer includes a low cross link SAP adapted to gel block upon wetting such that said backsheet is substantially impervious when wet and said backsheet is breathable when dry; and
   wherein said SAP are water-swellable particles included in a concentration in the range of about 50 g/m$^2$ to about 500 g/m$^2$.

2. The article of claim 1, wherein said nonwoven substrate is a section of said topsheet.

3. The absorbent article of claim 1, wherein said first absorbent composite is a prefabricated sheet.

4. The absorbent article of claim 3, wherein said first absorbent composite of said core includes a plurality of said absorbent layers, said layers being spaced apart from one another such that non-coated surface sections of said substrate are exposed therebetween.

5. The absorbent article of claim 4, wherein said non-coated surface sections form wicking zones between said absorbent layers.

6. The absorbent article of claim 1, wherein said first absorbent composite forms said backsheet and said core, said backsheet having a section providing said nonwoven substrate and said absorbent layer being concentrated at a crotch region of said backsheet to form said absorbent core.

7. The absorbent article of claim 1, wherein said first absorbent composite further includes a concentration of pulp material, said absorbent layer and said nonwoven substrate forming a sheet disposed about said pulp concentration such that said pulp concentration is disposed between at least two layers of said sheet of absorbent layer and nonwoven substrate.

8. The absorbent article of claim 1, wherein said first absorbent composite forms at least a portion of said topsheet and said absorbent core, said topsheet having a section providing said nonwoven substrate and said absorbent layer forming said core.

9. The absorbent article of claim 1, wherein said absorbent layer includes low-cross link, low gel strength SAP having free swell capacities of over 40 g/g and such that said absorbent layer is adapted to gel block upon wetting so as to be substantially impervious but is breathable when dry.

10. The disposable absorbent article of claim 1, wherein said non-swellable intersection between said absorbent core and each said longitudinally-extending absorbent composites, is a non-swellable, non-SAP coated band.

11. A disposable absorbent article comprising:
a topsheet;
a backsheet;
a pair of longitudinally-extending upstanding cuffs, each cuff having two sheet layers;
a continuous absorbent composite including
an absorbent layer of hydratable fine fibers in the form of microfibril obtained from cellulose or a derivative thereof, and absorbent polymer (SAP) particles bonded together by said hydratable fibers, and
a nonwoven substrate supporting said absorbent layer, said absorbent layer being coated thereupon; and
wherein said absorbent layer is disposed between said topsheet and said backsheet, and generally centrally at a location identified as a crotch region, said absorbent layer providing a swellable absorbent core for absorbing bodily exudates received in said crotch region; and
wherein said cuffs are spaced laterally from said absorbent core, and wherein said continuous absorbent composite includes two swellable longitudinally-extending composite sections extending upwardly from said crotch region into said cuffs and between the cuff layers, said continuous absorbent composite forming an absorbent structure about said crotch region; and
wherein said SAP are water-swellable bodies included in a concentration of about 20 gsm and said nonwoven substrate is a spunbond/meltblown/spunbond (SMS) having a basis weight in the range of about 10 gsm to 60 gsm; and
wherein each of said swellable absorbent core and two longitudinally-extending composite sections forms a distinct swellable SAP section of said continuous absorbent composite, said continuous absorbent composite being folded between said swellable absorbent core and each said longitudinally extending composite sections to form a substantially non-swellable intersection therebetween.

12. The disposable absorbent article of claim 11, wherein each said intersection is a non-swellable, non-SAP coated band.

13. The article of claim 11, wherein said absorbent layer is supported underneath a section of said topsheet, such that said section of said topsheet provides said nonwoven substrate.

14. The article of claim 11, wherein said absorbent layer is supported on said backsheet, such that a section of said backsheet provides said nonwoven substrate.

15. The article of claim 11, wherein said absorbent layer includes a low cross link SAP adapted to gel block upon wetting such that said backsheet is substantially impervious when wet and said backsheet is breathable when dry.

16. The absorbent article of claim 11, wherein said absorbent composite further includes a concentration of pulp material, said absorbent layer and said nonwoven substrate forming a sheet disposed about said pulp concentration such that said pulp concentration is disposed between at least two layers of said sheet of absorbent layer and nonwoven substrate.

17. In a disposable absorbent article having an absorbent core disposed between a topsheet and a backsheet, a pre-fabricated absorbent composite comprising:
an absorbent layer of hydratable fine fibers in the form of microfibril obtained from cellulose or a derivative thereof, and absorbent polymer (SAP) particles bonded together by said hydratable fibers, and
a nonwoven substrate supporting said absorbent layer, said absorbent layer being coated thereupon;
wherein said absorbent layer is disposed between said topsheet and said backsheet, and generally centrally in said article at a location identified as a crotch region, said absorbent layer providing an absorbent core for absorbing bodily exudates received by the crotch region; and
wherein said article includes a pair of longitudinally-extending, upstanding cuffs spiced laterally from said absorbent core, each cuff having two sheet layers, and wherein said absorbent composite includes two longitudinally-extending composite sections extending upwardly from the crotch region into said cuffs and between said cuff layers; and
wherein said absorbent layer includes a low cross link SAP adapted to gel block upon wetting such the said backsheet is substantially impervious when wet and the backsheet is breathable when dry; and
wherein each said longitudinally-extending composite sections and said absorbent core is a distinct swellable section of one continuous absorbent composite structure positioned about the crotch region, said continuous absorbent structure including folds providing an interface between each longitudinally-extending composite section and said absorbent core, each said interface being a non-SAP coated band that restricts swelling therearound.

18. The absorbent composite of claim 17, wherein said absorbent layer is supported underneath a section of said topsheet, such that said section of topsheet provides said nonwoven substrate.

19. The absorbent composite of claim 17, wherein said absorbent layer is supported on a section of said backsheet, such that said backsheet section provides said nonwoven substrate.

20. The absorbent composite of claim 17, wherein said low cross-link SAP is low-gel strength SAP characterized by a free swell capacity greater than about 40 g/g.

21. The absorbent composite of claim 17, wherein said SAP are water-swellable bodies included in a concentration of about 50 gsm to 500 gsm.

22. The absorbent composite of claim 17, further comprising a coating of mineral oil over said SAP particles of said absorbent layer, said coating being adapted to retard the initial receipt of liquid by said SAP in said absorbent layer.

* * * * *

UNITED STATES PATENT AND TRADEMARK OFFICE
CERTIFICATE OF CORRECTION

PATENT NO.    : 6,794,557 B1
DATED         : September 21, 2004
INVENTOR(S)   : Walter V. Klemp et al.

It is certified that error appears in the above-identified patent and that said Letters Patent is hereby corrected as shown below:

Column 1,
Line 31, delete "worm," and insert -- worn. --.
Line 37, delete "material" and insert -- materials --.

Column 3,
Line 34, after "dry", insert -- , --.
Line 64, delete "utilized" and insert -- utilize --.

Column 4,
Line 4, after "backsheet", insert -- , --.
Line 14, delete "by".
Line 26, delete "cross sectional" and insert -- cross-sectional --.

Column 5,
Line 3, delete "Invention." and insert -- invention; --.

Column 6,
Line 57, after "surface", and insert -- , --.
Line 58, delete "inside)" and insert -- inside --.
Line 59, delete "0.1" and insert -- 0.1% --.

Column 7,
Line 13, delete "pr" and insert -- or --.
Line 15, delete "particle" and insert -- Particle --.
Line 21, after "size", insert -- ,--.
Line 58, after "mm/Aq", insert -- mm/Aq, --.
Line 59, delete "mm/AQ," and insert -- mm/Aq, --.

Column 8,
Line 11, after "backsheet", insert -- , --.
Line 33, delete "AA" and insert -- A --.
Line 33, delete "BB" and insert -- B --.
Line 36, delete "AA" and insert -- A --.

Column 10,
Line 31, delete "surface (s)" and insert -- surface(s) --.
Line 48, after "50", insert -- . --.
Line 48, delete "such" and insert -- - --
Line 55, delete "in" and insert -- and --.

UNITED STATES PATENT AND TRADEMARK OFFICE
CERTIFICATE OF CORRECTION

PATENT NO. : 6,794,557 B1
DATED : September 21, 2004
INVENTOR(S) : Walter V. Klemp et al.

It is certified that error appears in the above-identified patent and that said Letters Patent is hereby corrected as shown below:

Column 11,
Line 58, delete "space-apart" and insert -- spaced-apart --.

Column 14,
Line 1, delete "1833" and insert -- 1903 --.
Line 18, after "instead" insert -- , --.
Line 26, delete "an" and insert -- a --.

Column 16,
Line 6, delete "region)" and insert -- region --.

Column 17,
Line 31, delete "The" and insert -- the --.

Column 18,
Line 15, delete "an".

Column 19,
Line 7, delete "composites," and insert -- composite, --.

Column 20,
Line 23, delete "spiced" and insert -- spaced --.
Line 31, delete "the" and insert -- that --.

Signed and Sealed this

Twenty-third Day of November, 2004

JON W. DUDAS
*Director of the United States Patent and Trademark Office*